US00PP19369P2

(12) United States Plant Patent
Riddle

(10) Patent No.: US PP19,369 P2
(45) Date of Patent: Oct. 21, 2008

(54) ALMOND TREE NAMED 'CAPITOLA'

(50) Latin Name: *Prunus dulcis*
Varietal Denomination: Capitola

(76) Inventor: Robert L. Riddle, 12013 El Pomar Ave., Waterford, CA (US) 95386

( * ) Notice: Subject to any disclaimer, the term of this patent is extended or adjusted under 35 U.S.C. 154(b) by 0 days.

(21) Appl. No.: 12/008,813

(22) Filed: Jan. 14, 2008

(51) Int. Cl.
*A01H 5/00* (2006.01)

(52) U.S. Cl. ..... Plt./155

(58) Field of Classification Search ..... Plt./155
See application file for complete search history.

*Primary Examiner*—Annette H Para
(74) *Attorney, Agent, or Firm*—Wells St. John P.S.

(57) ABSTRACT

A new and distinct variety of almond tree as described, and which is somewhat similar to the 'Nonpariel' almond tree (unpatented), but which is distinguishable therefrom by producing a small to medium sized kernel of high quality and having a sweet flavor.

1 Drawing Sheet

BACKGROUND OF THE NEW VARIETY

The present invention relates to a new and distinct variety of almond tree, *Prunus dulcis* which will hereinafter be denominated varietally as 'Capitola,' and more specifically to an almond tree which produces a crop for harvesting and shipment approximately mid-August under the ecological conditions prevailing in the Waterford area of the San Joaquin Valley of central California.

It has long been recognized that it would be desirable to provide almond trees bearing a crop which is ripe for commercial harvesting and shipment during the middle of August under the ecological conditions prevailing in the San Joaquin Valley of central California. In this regard, several varieties are harvested during this time period. These varieties include the 'Nonpariel' almond tree (unpatented), and the 'Carmel' almond tree, U.S. Pat. No. 2,641. In relative comparison with these two well known varieties of almond trees which are harvested in the same season, the present variety produces a nut crop which has a shell which is softer than that produced by the 'Carmel' almond tree variety, but which is not as soft as that produced by the 'Nonpariel' almond tree variety. Still further, the present variety is distinguishable from the foregoing almond tree varieties by producing a kernel having a characteristically sweet flavor.

In the evaluation of almond tree varieties, a number of criteria are utilized to determine whether a new almond tree variety will have commercial success. As a general matter, new trees and their crops are usually evaluated on the basis of their ripening date, flavor, texture, storage and shipping quality. With almond trees, for example, the early ripening date and the quality of meat of the kernel, freedom from unusual numbers of doubles (the production of double kernels) as well as a soft shell, typically makes such almond tree varieties commercially attractive. It has long been known that almond tree varieties that produce soft shell almonds are more commercially attractive because they are easier to shell. Still further, a variety that produces a low percentage of doubles provides a degree of appeal to distributors and consumers.

ORIGIN AND ASEXUAL REPRODUCTION

The present variety of almond tree was discovered by the inventor in early 1980 as a chance seedling, of unknown parentage, then growing within a cultivated region which was adjacent to his 'Nonpariel' (unpatented) almond orchard which is located in Waterford, Calif. After more than a dozen years of observation, the inventor proceeded, in 1992, to asexually propagate the new variety of almond tree by grafting wood of the new variety onto 'Nemaguard' rootstock (unpatented), that was then growing in his orchard which was located in Waterford, Calif. In addition to this first asexual reproduction, a number of other trees were also asexually propagated by grafting onto 'Nemaguard' rootstock (unpatented), and planted, in 1999, at a commercial orchard which is located in Oakdale, Calif. In the 15 years which have passed since the first asexual reproduction took place in 1992, the inventor has observed the subject trees, as well as compared and contrasted the reproduced tree and the crop produced by same, against the original chance seedling, and he has determined that the asexually reproduced trees are true to the original chance seedling.

SUMMARY OF THE VARIETY

The 'Capitola' almond tree is characterized principally as to novelty by producing a consistently good quality nut crop which is soft shelled, well sealed, and which resembles, in some respects, the crop produced by the 'Nonperiel' almond tree (unpatented). More specifically, the present variety produces a crop which is mature for commercial harvesting, hulling, shelling, and shipment approximately August 10–August 15 under the ecological conditions prevailing in Waterford, Calif. In relative comparison to the crop produced by the 'Nonpariel' almond tree (unpatented), the almonds produced by the 'Capitola' almond variety produces a smaller, slightly darker kernel of higher quality when compared to the 'Nonpariel' almond tree (unpatented). Still further, the shell of the 'Capitola' variety, while soft, is not as soft as that of the 'Nonpariel' almond tree (unpatented). Still further, the nuts produced by the 'Capitola' almond tree have a very low percentage of doubles as compared to the nut crop produced by the 'Nonpariel' almond tree (unpatented) as disclosed in greater detail hereinafter.

BRIEF DESCRIPTION OF THE DRAWING

The accompanying drawing which is provided is a color photograph of the new variety of almond tree. The photograph depicts two branches of the present variety displaying its growth characteristics with almonds sufficiently matured for harvesting and shipment. Further, a twig bearing typical leaves showing the dorsal and ventral coloration thereof is also depicted. Additionally, six shelled almonds and kernels are shown and which display the side view; overall shape; and suture characteristics thereof. The colors in this photograph are as nearly true as is reasonably possible on a color representation of this type. Due to chemical development, processing, and printing, the leaves and nut crop depicted in these photographs may or may not be accurate when compared to the actual specimen. For this reason, future color references should be made to the color plates as provided by The Royal Horticultural Society Colour Chart, 3rd Edition.

DETAILED DESCRIPTION

Referring more specifically to the botanical details of this new and distinct variety of almond tree, the following has been observed during the 15th growing season under the ecological conditions prevailing at the orchard of the inventor which is located near Waterford, Calif. All major color code designations are by reference to the R.H.S. Colour Chart, 3rd Edition provided by The Royal Horticultural Society of Great Britain. Common color names may also be occasionally used.

NOT A COMMERCIAL WARRANTY

The following detailed description has been prepared to solely comply with the provisions of 35 U.S.C. § 112, and does not constitute a commercial warranty, (either expressed or implied), that the present variety will in the future display the botanical or other varietal characteristics as set forth, hereinafter. Therefore, this disclosure may not be relied upon to support any future legal claims including, but not limited to, breach of warranty of merchantability, or fitness for any particular purpose which is directed, in whole, or in part, to the present variety.

TREE

*Origin.*—The present variety was discovered as an open pollinated seedling of unknown parentage growing within the cultivated region adjacent to the inventor's orchard which is located in Waterford, Calif.

*Vigor.*—Considered vigorous.

*Hardiness.*—Considered hardy under typical San Joaquin Valley climatic conditions.

*Chilling requirement.*—Considered normal under prevailing San Joaquin Valley climatic conditions.

*Tree form.*—Considered spreading and upright in its growth pattern. For observed trees that were 15 years old, the height of the trees were approximately 10–13 feet. Further, these same trees had a crown spread of approximately 10–14 feet.

*Crotch angle.*—Generally — Approximately 52 degrees.

*Productivity.*—Considered very productive. For trees that are at least 5 years old, with currently acceptable planting densities, approximately 1500 pounds of almonds are harvested per acre.

*Regularity of bearing.*—Considered regular for the species.

TRUNK

*Size.*—Considered large, approximately 24.75 inches in circumference when measured at a distance of about 16 inches above the surface of the earth on trees which are at least 15 years old.

*Bark texture.*—Considered rough.

*Bark color.*—Grey-green (RHS 189C).

*Bark lenticels.*—Numbers — Few. This characteristic is not distinctive of the present variety.

BRANCHES

*Size.*—Considered large for the species, approximately 12.5 inches in circumference when measured at a distance of approximately 12 inches above the crotch of the tree.

*Surface texture.*—Immature branches — Considered smooth.

*Surface texture.*—Mature branches — Slightly rough.

*Bark color.*—One year or older wood, Grey-red (RHS 187A).

*Bark color.*—Immature branches — Green (RHS 139C).

*Lenticels.*—Size and Number — Primary scaffold branches — Approximately 6–8 mm in diameter. Approximately 18–20 lenticels may be found over any 4 inch length of a primary scaffold branch.

LEAVES

*Size.*—Considered large for the species, approximately 75 mm to about 125 mm in length; and about 21 mm. to about 36 mm. in width.

*Leaf shape.*—Considered lanceolate.

*Leaf thickness.*—Normal for almond tree leaves.

*Leaf color.*—Upwardly facing surfaces — Green (RHS 136B).

*Leaf color.*—Downwardly facing surfaces — Green (RHS 137B).

*Leaf marginal form.*—Crenulate.

*Leaf vein.*—Color — Yellow (RHS 145C).

*Leaf vein.*—Thickness — About 2 mm.

*Leaf gland numbers.*—0.

*Leaf petiole.*—Length — About 25 mm. to about 43 mm.

*Leaf petiole.*—Thickness — About 2 mm.

*Leaf petiole.*—Color — Yellow (RHS 145C).

*Petiole sinus.*—Shape — Rounded at the base.

*Leaf stipules.*—Numbers — 1–3 small leaf stipules will be found.

*Leaf stipules.*—Size — About 2 mm.

*Leaf stipules.*—Color — Grey-orange (RHS 177A).

*Leaf stipules arrangement.*—Opposite.

FLOWER

*Date of full bloom.*—Feb. 26, 2007 under the ecological conditions prevailing near Waterford, Calif.

*Bloom amount.*—Generally considered abundant. 1 or 2 flowers are produced at each node.

*Bloom color.*—Light pink (RHS 69C).

*Flower diameter.*—Approximately 36 mm. to about 42 mm.

*Petals.*—Marginal form — Considered undulate with some apex notching being evident.

*Petals.*—Length — About 16 mm. to about 22 mm.

*Petals.*—Width — About 11 mm. to about 14 mm.

*Sepals.*—Numbers — 5.

*Sepals.*—Color — Generally green (RHS 144B), however, a grey-orange color (RHS 183C) may be detected at the upper end.

*Size of individual sepals.*—Approximately 6.5 mm. to about 8 mm. in length and about 5 mm. in width.
*Sepals.*—Shape — Conic.
*Pistil.*—Length — About 11 mm. to about 14 mm.
*Pistil.*—Color — Generally green-white (RHS 155A); however, a grey-yellow color (RHS 160D) appears in the upper half.
*Anthers.*—Length — About 1.5 mm.
*Anthers.*—Color — Grey-yellow (RHS 162A).
*Pollen production.*—Abundant.
*Pollen color.*—Yellow-orange (RHS 15B).
*Stamens.*—Length — About 5 mm. to about 12 mm.
*Stamens.*—Color — Grey-white (RHS 155C). With increasing senescence, the basal ends become increasingly pink (RHS 63B).
*Pedicel.*—Length — About 1.5 mm. to about 2.5 mm.
*Pedicel.*—Width — About 1 mm. to about 1.45 mm.
*Pedicel.*—Color — Yellow-green (RHS 144B).
*Flower buds.*—Diameter — About 2 mm. to about 4 mm.
*Flower buds.*—Length — About 2 mm. to about 4 mm.
*Flower buds.*—Shape — Generally considered conic.
*Flower buds.*—Color — Grey-orange (RHS 75A).
*Bud scale.*—Color — Grey-orange (RHS 165B).

CROP

*Bearing.*—Considered regular.
*Harvesting.*—Approximately August 10–August 15 under the ecological conditions prevailing near Waterford, Calif.
*Productivity.*—Considered productive and very good for trees that are 5 years old.
*Distribution of nuts on the tree.*—Well distributed throughout.
*Tenacity.*—Considered good for the species.
*Hull.*—Texture — Considered slightly pubescent.
*Pits.*—None are evident.
*Hull.*—Form — Considered ovate.
*Hull.*—Thickness — About 23 mm. to about 25 mm.
*Hull.*—Suture — Generally — Considered pronounced.
*Hull.*—Color — Grey-green (RHS 189B).
*Dehiscence.*—Considered good for this variety.
*Splitting.*—Considered good for this species.

NUT

*Nut size.*—Generally — Length — About 26.9 mm. to about 28.75 mm.; Width — about 1.0 mm. to about 1.12 mm.
*Shape.*—Considered ovate.
*Thickness.*—About 14.3 mm.
*Outer shell.*—Form — Considered flaked.
*Inner shell.*—Form — Considered brittle.
*Color.*—Grey-yellow (RHS 162B).
*Pits.*—Present, but considered scattered.
*Stem attachment point.*—Considered minimal and small and is not prominent relative to the nut.
*Apex.*—Shape — Pointed.
*Wing.*—Inner Surface Texture — Considered smooth.
*Percent of kernel relative to the overall nut.*—Approximately 57.27 percent to about 60.96 percent.
*Hull thickness.*—About 3 mm.

KERNEL

*Size.*—Length — About 21 mm. to about 23 mm.; and about 13 mm. in width.
*Shape.*—Ovate.
*Kernel thickness.*—About 9 mm to about 12 mm.
*Bark.*—Shape — Considered slightly rounded.
*Stem scar.*—Not readily apparent.
*Apex.*—Shape — Considered acute.
*Surface texture.*—Slightly ribbed.
*Pubescence.*—Not evident.
*Color.*—Grey-orange (RHS N171B).
*Numbers of doubles produced.*—Of 130 specimens, 3 of the specimens included doubles. This is a 2.3 percent rate. This is low in relative comparison to the amount of doubles produced by the 'Nonpariel' almond trees (unpatented) which are growing in the same geographical location.
*Kernel flavor.*—Sweet and considered very good and superior to that of the 'Nonpariel' almond trees (unpatented) which are growing in the same geographical location.
*Keeping quality.*—Considered very good. The crop is useful for fresh market applications.
*Keeping and shipping quality.*—Considered good for the variety.
*Resistance to disease.*—The present variety appears resistant to anthracnose. Still further, in view of the well sealed nut, there is minimal insect infestation of the crop.
*Pollination requirement.*—The present variety appears to require pollination by a variety similar to the 'Nonpariel' almond tree (unpatented).
*Average kernel weight.*—About 24 average weight per ounce.
*Kernel size.*—In relative comparison to the kernels produced by the 'Nonpariel' almond tree (unpatented), the kernels of the present variety are smaller and slightly darker in color, and further have a flavor characteristic that is sweet and distinctive from the crop produced by the 'Nonpariel' almond tree (unpatented) growing in the same geographical area. Still further, in view of the low percentage of doubles that the present variety produces, this new variety of almond tree would appear to be quite distinctive and novel in relative comparison to the 'Nonpariel' almond trees (unpatented) which growing in the same geographical area, and which are mature for harvesting in the same season.

Although this new variety of almond tree possesses the described characteristics, noted above, as a result of the growing conditions prevailing in the central part of the San Joaquin Valley of central California, it is to be understood that variations of the usual magnitude and characteristics incident to changes in growing conditions, fertilization, pruning and pest control are to be expected.

Having thus described and illustrated my new variety of almond tree, what I claim is new, and desire to secure by Plant Letters Patent is:

1. A new and distinct variety of almond tree as substantially shown and described, and which is somewhat similar to the 'Nonpariel' almond tree (unpatented), but which is distinguishable therefrom by producing a smaller, slightly darker kernel of high quality with a soft shell and which has a crop which is comparatively free of doubles.

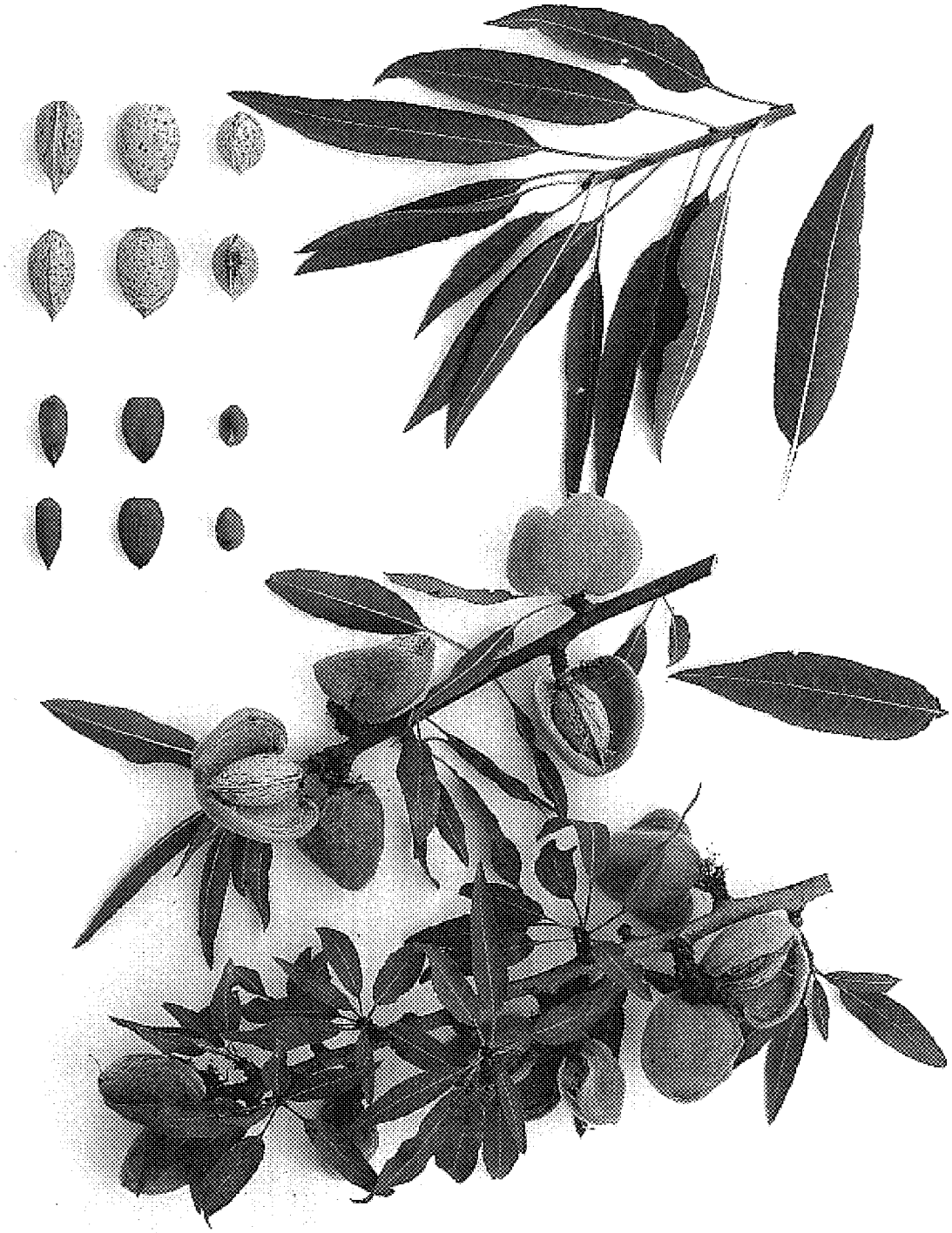

* * * * *